(12) United States Patent
Öerter

(10) Patent No.: US 9,360,003 B2
(45) Date of Patent: Jun. 7, 2016

(54) MAGNETICALLY ACTUATED DISPOSABLE CARTRIDGE PUMP, A PUMP SYSTEM, AND A METHOD OF PUMPING

(75) Inventor: Göekhan Öerter, Weilmünster (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 348 days.

(21) Appl. No.: 13/391,472

(22) PCT Filed: Aug. 17, 2010

(86) PCT No.: PCT/EP2010/005064
§ 371 (c)(1),
(2), (4) Date: Feb. 21, 2012

(87) PCT Pub. No.: WO2011/020600
PCT Pub. Date: Feb. 24, 2011

(65) Prior Publication Data
US 2012/0177506 A1    Jul. 12, 2012

(30) Foreign Application Priority Data
Aug. 18, 2009  (DE) .......................... 10 2009 037 845

(51) Int. Cl.
*F04B 43/04* (2006.01)
*F04B 43/00* (2006.01)
(Continued)

(52) U.S. Cl.
CPC .............. *F04B 43/04* (2013.01); *A61M 1/1053* (2013.01); *A61M 1/1055* (2014.02);
(Continued)

(58) Field of Classification Search
CPC ........ F04B 43/00; F04B 17/04; F04B 43/042; F04B 43/02; F04B 43/0054; F04B 43/0063; F04B 43/04; F04B 43/046; F04B 43/14; F04B 45/04; F04B 45/047; F04B 17/042; F04B 17/044; F04B 43/06; F04B 43/009; F04B 45/053; F16J 3/048; F16J 3/02
USPC .................................. 417/53, 322, 412, 413.1
See application file for complete search history.

(56) References Cited

U.S. PATENT DOCUMENTS

| 4,459,977 A | 7/1984 | Pizon et al. |
| 4,498,850 A | 2/1985 | Perlov et al. |

(Continued)

FOREIGN PATENT DOCUMENTS

| DE | 589398 | * 9/1933 | .............. F04B 39/10 |
| DE | 589 398 | 12/1933 | |

(Continued)

OTHER PUBLICATIONS

Internation Search Report (ISR) PCT/EP2010?005064 (Nov. 15, 2010).*

(Continued)

*Primary Examiner* — Bryan Lettman
*Assistant Examiner* — Timothy P Solak
(74) *Attorney, Agent, or Firm* — Jacobson Holman, PLLC.

(57) ABSTRACT

A disposable pump element has at least one first part, in which channel structures are recessed in the surface, and a second part sealingly covering the first part. A larger portion of the first part is applied to a rigid carrier structure. The first part has at least one flexible region, and at the flexible region thereof, the first part is not applied to the rigid carrier structure. A system for pumping, and a method for pumping a liquid, both employ the disposable pump element.

20 Claims, 1 Drawing Sheet

(51) Int. Cl.
*F04B 45/047* (2006.01)
*F04B 17/04* (2006.01)
*F16J 3/02* (2006.01)
*A61M 1/10* (2006.01)
*F04B 43/02* (2006.01)
*A61M 1/14* (2006.01)

(52) U.S. Cl.
CPC .......... *F04B 17/044* (2013.01); *F04B 43/0063* (2013.01); *F04B 43/02* (2013.01); *F04B 45/047* (2013.01); *F16J 3/02* (2013.01); *A61M 1/14* (2013.01); *A61M 2205/12* (2013.01)

(56) References Cited

U.S. PATENT DOCUMENTS

| | | | |
|---|---|---|---|
| 4,638,196 A * | 1/1987 | Kranzler | H02K 5/148 310/50 |
| 4,826,131 A * | 5/1989 | Mikkor | 251/129.17 |
| 5,011,380 A * | 4/1991 | Kovacs | B29C 33/40 417/413.1 |
| 5,074,765 A * | 12/1991 | Pekar | F04B 45/04 36/29 |
| 6,261,065 B1 | 7/2001 | Nayak et al. | |
| 7,198,250 B2 * | 4/2007 | East | F04B 43/046 258/129.06 |
| 2002/0098122 A1 | 7/2002 | Singh et al. | |
| 2003/0180164 A1 * | 9/2003 | Bunner et al. | 417/413.1 |
| 2004/0265150 A1 | 12/2004 | McElfresh et al. | |
| 2006/0013710 A1 * | 1/2006 | Lee | 417/413.1 |
| 2007/0278155 A1 * | 12/2007 | Lo | A61M 1/16 210/646 |
| 2009/0169402 A1 * | 7/2009 | Stenberg | 417/413.1 |
| 2011/0070132 A1 | 3/2011 | Haecker et al. | |

FOREIGN PATENT DOCUMENTS

| | | | |
|---|---|---|---|
| DE | 31 16 765 | 10/1990 | |
| DE | 41 18 628 | 2/1992 | |
| DE | 199 63 306 | 8/2001 | |
| DE | 102 39 597 | 3/2004 | |
| EP | 0 024 431 | 3/1981 | |
| WO | WO 80/01934 | 9/1980 | |
| WO | WO80/01934 | * 9/1980 | F04B 43/08 |
| WO | 2006/123329 | * 11/2006 | A61B 8/14 |
| WO | WO 2006/123329 | 11/2006 | |

OTHER PUBLICATIONS

German Office Action 10 2009 037 845.6-15 (Jan. 11, 2010).*

* cited by examiner

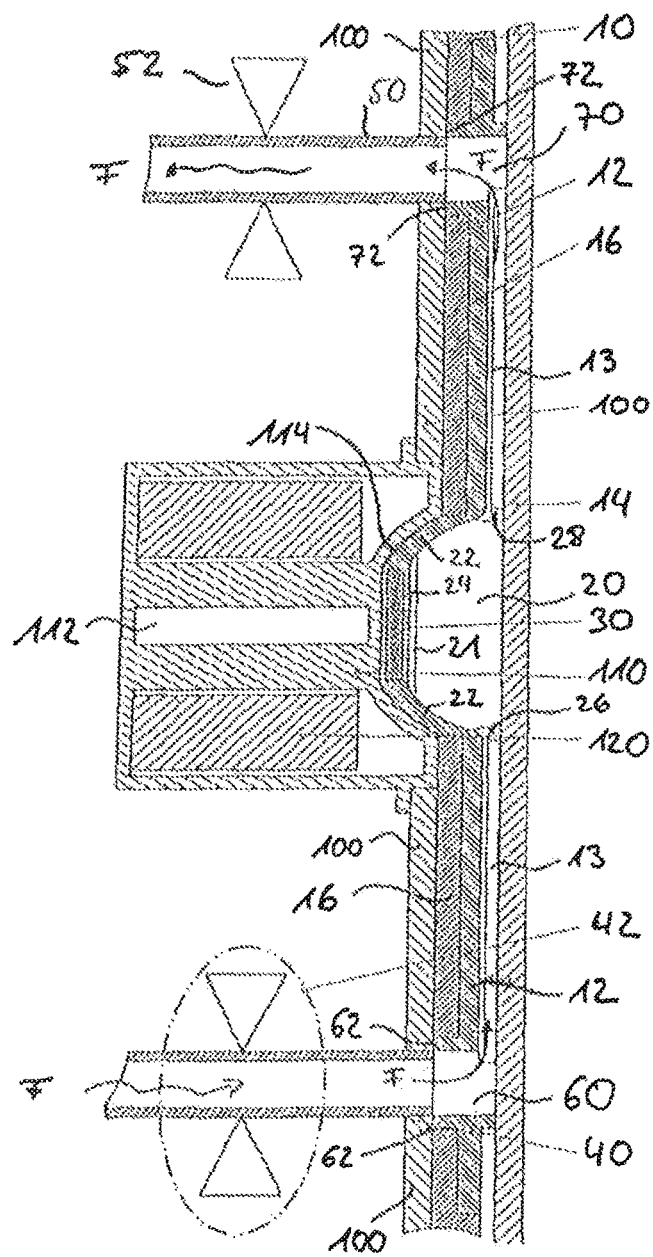

MAGNETICALLY ACTUATED DISPOSABLE CARTRIDGE PUMP, A PUMP SYSTEM, AND A METHOD OF PUMPING

CROSS-REFERENCE TO RELATED APPLICATIONS

This is a national of PCT/EP10/005064 filed Aug. 17, 2010 and published in German, which claims the priority of German number 10 2009 037 845.6 filed Aug. 18, 2009, hereby incorporated by reference.

BACKGROUND OF THE INVENTION

1. Field of Invention

The present invention relates to a disposable element comprising at least one first part, in which channel structures are recessed in the surface, and a second part sealingly covering said first part, with the larger part of the first part and/or of the second part being made rigid and/or being applied to a rigid carrier structure, and with these first and/or second parts, however, having at least one flexibly made region. The invention furthermore relates to a system for pumping and a method for pumping a liquid.

2. Description of the Prior Act

Disposable cassettes are already known from the prior art which are preferably used in the area of analytical technology. These cassettes have, for example, a plurality of layers which have rigid and flexible regions and which are made in one piece using two-component injection molding technology. The flexible regions can be made, for example, as pump chambers which can be pushed in by a corresponding actuator so that a fluid displacement takes place. A pump movement and/or also corresponding valve functions in the flexible regions is/are thus generated by mechanically driven plungers. Such mechanical interfaces, however, cause problems in the coupling of the disposable cassette to a corresponding machine. On the one hand, the so-called disposable cannot be placed completely smoothly on the machine part since there are always projections or recesses of the mechanical interfaces. On the other hand, a mechanical activation of the membranes can cause damage, for instance by the mechanical flexing movements of the flexible regions, which can result in the failure of the component. Such a corresponding disposable cassette is known, for example, from DE 102 39 597 A1.

U.S. Pat. No. 6,261,065 B1 furthermore describes a blood treatment system which is connected to a blood separation unit. This system has a cassette which has at least one pneumatically actuated pump.

U.S. 2007/0278155 A1 describes a mechanical fluid system having disposable cassettes which have flexible layers. Balance chamber systems for very precise liquid balancing are described which have first and second pump chambers and are separated by a flexible membrane. The inflow of a first fluid quantity into a first chamber of the balance chamber causes the displacement of the corresponding quantity of fluid from the second chamber. For this balance pump movement, a permanent magnet can be worked onto the flexible membrane which separates the two chambers and which can be moved by external electromagnets.

An electromagnetically operated membrane pump is furthermore known from DE 58 93 98 which is in particular provided for the aeration of aquariums. A magnetic armature is brought to oscillation by means of an electromagnet so that an air blast can be generated which can be introduced into the aquarium by means of a pressure pipe.

A drive for blood pumps is known from DE 199 63 306 A1 which is made in the form of a loudspeaker drive. In this connection, the drive has a magnet system and a mechanically sliding piston which is controlled by an absolute-position encoder and has windings which can be switched over and/or off, in which magnet system the piston can be fixed mechanically.

U.S. Pat. No. 4,459,977 relates to an apparatus for dialostic blood retroperfusion which can have an electromagnetically operated membrane pump.

U.S. Pat. No. 4,498,850 describes a pump having a pump chamber recess which is divided into two chambers by a magnetically actuable membrane and which is let into a pump chamber housing. A plurality of means are provided around the recess by means of which a magnetic field is applied so that the magnetically actuable membrane can be moved to trigger a pump movement.

WO 2006/123329 A2 describes a dispensing apparatus for a therapeutic fluid, in particular a dispensing apparatus for insulin, which is easy to handle and is preferably made in credit-card format. A membrane pump is described in connection with this apparatus which cooperates with two membrane valves which are each disposed upstream and are likewise activated electromagnetically.

SUMMARY OF THE INVENTION

It is therefore the object of the present invention to further develop a disposable element of the initially named kind in an advantageous manner, in particular such that it can be actuated in a contactless manner, can be operated simply and safely and is able to pump liquids, in particular medical liquids, highly precisely.

This object is solved in accordance with the invention by a disposable element having the features described herein. Provision is accordingly made that a disposable element is made of at least one first part, in which channel structures are recessed in the surface, and a second part sealingly covering said first part, with the larger part of the first part and/or of the second part being made rigid and/or being applied to a rigid carrier structure, and with these first and/or second parts, however, having at least one flexibly made region. Provision is further made that the at least one flexible region has at least one permanent magnet and/or at least one permanent magnetic region so that liquid can be displaced by means of the flexible region by application of a magnetic field.

The advantage thereby results that now no mechanical interface with a machine part which drives the flexible region is necessary for the generation of the movement of the flexible region by the permanent magnet. It is rather now possible to act on the flexible region in a contactless manner to be able to displace liquid hereby. Due to the omission of the plungers which had previously acted on corresponding flexible regions of known disposable elements, such as disposable cassettes, the coupling of the disposable element in accordance with the invention to a corresponding machine is simplified. Because now a substantially smooth application to the corresponding machine part is possible since a correspondingly smoothed, matched surface can be provided due to the omission of the mechanical, movable interface components. Furthermore, mechanical damage can no longer occur due to the contactless activation, which minimizes the failure probability of the component. The advantage furthermore results that the energy consumption for the activation of a pump, which can be formed by the flexible region, for example, can be reduced. The advantage further results that the corresponding apparatus into which the disposable element can be inserted can now be made more simply and compact.

It is conceivable that conventional thermoplastic elastomers are used for the flexible region. Polymer blends of SEBS (i.e., Styrene Ethylene Butylene Styrene) and PP (i.e., Polypropylene) can preferably be used. These blends have the advantage that they can be steam sterilized. It is alternatively conceivable that other blends can also be used provided they are compatible with the common sterilization methods in medical engineering. It is conceivable that the first and second parts are made in layer form. The carrier structure can also be made in layer form and can, for example, carry the part which is formed as a completely flexible layer and in which channel structures are formed. It is advantageously conceivable in this connection that the first part forms a middle layer which is enclosed in sandwich form by the carrier structure on the one side and by the sealingly covering second layer, which is formed by the second part, on the other side.

Provision can furthermore be made that the disposable element is manufactured by a process in which rigid and flexible regions of the first and/or second part are manufactured in one piece by means of two-component injection molding.

It is furthermore advantageously conceivable that the carrier structure and/or the first and/or second part are manufactured in one piece by means of two-component injection molding. The advantage thereby results of being able to make the advantageous structure of the disposable element with rigid and flexible regions cost-effectively and simply in only one single injection molding procedure.

Provision can furthermore be made that the at least one flexible region with the permanent magnet and/or the permanent magnetic region is made in chamber-like or dome-like form. It is, for example, conceivable in this connection that the chamber base is formed by the second part which sealingly covers the first part. The advantage thereby results that a fluid-dynamically favorable and simultaneously simply realizable pump chamber can be formed.

It is of advantage if the flexible region made in chamber-like form is a pump chamber of a membrane pump.

Provision can furthermore be made that the flexible region has at least one inflow and at least one outflow, with the inflow and the outflow each being formed by a channel structure and/or being connected to a channel structure. It is conceivable in this connection that a respective valve element is present in the region or in functional relationship with the inflow and outflow so that the flexible region can be used as a membrane pump. Provision can thus be made for the suction phase of the pump chamber of the membrane pump that the valve element is closed in the outflow and the valve element is open in the inflow. The valve element is then closed in the inflow and open in the outflow for the ejection phase.

It is furthermore conceivable that the permanent magnet and/or that the permanent magnetic part is an insertion part which is completely encased by the flexible region. The advantage thereby results that such an insertion part can be inserted into the injection molding tool before the plastic injection molding, in particular before the start of the two-component injection molding, and is then completely encased by the flexible portion of the disposable element during production. It thereby becomes possible to work the permanent magnet and/or the permanent magnetic region simply into the pump segment and furthermore to achieve the advantage that the permanent magnet and/or the permanent magnetic region has no fluid contact due to its casing.

Provision can furthermore be made that the permanent magnet and/or the permanent magnetic region is arranged in a part of the flexible region which is disposed opposite a wall so that the flexible region is movable in the direction of the wall by application of a magnetic field with a first orientation and/or so that the flexible region is movable away from the wall by application of a magnetic field with a second orientation. The wall can advantageously be a region of the second part. It is conceivable in this respect that a reduction of the pump chamber volume takes place on application of a magnetic field in the first orientation and a restoration of the chamber walls takes place on the application of the magnetic field with the second orientation and the pump chamber is again also already in the suction phase in this step.

It is furthermore possible that the flexible region has a side wall which is made peripherally concave and which has a diameter reducing toward the region with the permanent magnet and/or the permanent magnetic region. This can advantageously be realized in that the flexible region is a dome-like pump chamber of a membrane pump made substantially round. In this case, the region with the permanent magnet and/or the permanent magnetic region is arranged in the upper region of the chamber when the wall, which is made by the second part of the disposable element, for example, is considered as a chamber base.

Provision can advantageously be made that the side wall is resilient and opposes a pressing in of the flexible region with a resilient force which effects a self-restoration of the flexible region on load removal. The flexible region or the membrane of the membrane pump can therefore be made such that a material tension is built up on the activation from its rest position in the membrane or in the side walls of the membrane so that a restoration force is simultaneously adopted. Due to the application of the magnetic field, the membrane only has to be pressed in to generate a pump function so that a magnetic field only has to be applied in one single deflection direction. The correspondingly opposing movement for the restoration then takes place solely from the restoration force of the flexible region or of the membrane. A pole reversal of the magnetic field is thus not necessary.

The restoration movement of the membrane can, however, as already described above, likewise be supported by a reversed magnetic field. This is, however, preferably only possible when a permanent magnet is used as the magnetic element in the membrane. The membrane can thus only be operated continuously with a homogeneous force profile from one side.

The present invention furthermore relates to a system for pumping having the features described herein. Provision is accordingly made that a system for pumping has a disposable element as described herein as well as a reception apparatus into which the disposable element can be inserted. In this respect, the system has at least one means for the generation of a magnetic field by means of which the flexible region of the disposable element is movable with the at least one permanent magnet and/or at least one permanent magnetic region.

Provision can furthermore be made that the reception apparatus engages in a shaped-matched manner around the disposable element and/or that the means for the generation of a magnetic field is an electromagnetic coil, preferably an electromagnetic coil provided with an iron core, with the electromagnetic coil being arranged in a housing with a receiver for the flexible region.

A sinusoidal voltage characteristic is of advantage for the control of the electromagnet in alternating field operation. Voltage peaks can thus be avoided which could cause damage to the electronics of the system. Other voltage characteristics are likewise conceivable if an improved pump performance should be achieved.

The pumping movement of the membrane is advantageously correlated with further functional parts of the machine side or of the disposable element. The membrane position can in particular be regulated to the disposable element with valve units. In accordance with a corresponding arrangement, liquids can thus be pumped or sucked.

The advantage furthermore results from an electromagnetic control that the system is able to control the pump rate. The pump rate can also be varied by an electric regulation and can react to instructions of a corresponding control unit. It is conceivable in this connection that the system has corresponding regulation and/or control means. It is furthermore conceivable that conclusions can be drawn on the pump power via a calibration or on the basis of already known volume ratios and with reference to the electric control. It thereby becomes possible to achieve a very exact balancing of the conveyed liquid volume.

It is particularly advantageous if the system is a blood treatment apparatus, in particular a dialysis machine. Provision can equally be made that it is an analysis unit.

The present invention furthermore relates to a method for pumping a liquid as described herein. Provision is accordingly made that, in a method for the pumping of a liquid by application of a magnetic field, a flexible region with at least one permanent magnet and/or with at least one permanent magnetic region of a disposable element displaces the liquid. In this respect, the disposable element comprises at least one first part in which channel structures are recessed in the surface and a second part sealingly covering it, with the larger part of the first part and/or of the second part being made rigid and/or being applied to a rigid carrier structure and with these first and/or second parts, however, having at least one flexibly made region.

It is particularly advantageous if the method is carried out using a disposable element having the features described herein and/or using a system having the features described herein.

BRIEF DESCRIPTION OF THE DRAWINGS

Further details and advantages of the invention will now be explained in more detail with reference to an embodiment shown in the drawing. There is shown:

The drawing figure provides a schematic sectional representation through a system for the pumping of liquids.

DETAILED DESCRIPTION OF THE PREFERRED EMBODIMENTS

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

The drawing figure shows, in section, a system in accordance with the invention for the pumping of liquids, wherein a disposable element 10 is received into the reception apparatus of the system otherwise only shown by the housing 110 with a receiver 114 and the electromagnetic coil 120.

The disposable element 10 has a flexible first part 12, which is made as a flexible layer. Channel structures 13 are recessed in the flexible first part 12 which are sealed by the second part 14, which is made as a rigid cassette base. The flexible first part 12 is carried by a rigid carrier structure 16 so that the flexible first part 12 is enclosed between the rigid carrier structure 16 and the second part 14. The disposable element 10 is in this respect partly made in the two-component injection molding process, with the flexible first part 12 and the rigid carrier structure 16 being made in the two-component injection molding process. The second part 14 is adhered subsequently. It is also conceivable that the second part 14 is formed by a sheet.

The disposable element 10 is in this respect made as a disposable cassette 10.

The pump chamber 20 of an electromagnetically actuated membrane pump is located in the middle region of the disposable cassette 10. The pump membrane 21 is a flexible region 21 which is a part of the flexible part 12; i.e., of the flexible layer. The flexible region 21 in this respect rises in dome-like form from the flexible first part 12 and passes through the rigid carrier structure 16. The pump membrane 21 has side walls 22 which are made from flexible elastomer and which can preferably be made as side walls 22 in a peripherally circularly continuous manner. The pump chamber 20 is made round, preferably circular, in such a case. If it is assumed that the chamber base is formed by the layer 14, i.e., the second part 14 of the disposable element 10, the pump chamber roof is formed by the wall region 24 of the flexible region 21.

The disposable cassette 10 can generally be oriented as desired with the pump chamber 20, that is can be inserted and operated, for instance, in a perpendicular, horizontal or slanted alignment in a corresponding receiver. The functionality of the membrane pump is not impaired by this.

The permanent magnet 30, which is completely encased by the flexible region 21, is located in this wall region 24. Due to the flexible structure and the dome-like geometry of the pump membrane 21, it is self-restoring, that is, the pump membrane 21 always returns to the zero position shown in the drawing figure by resilience in the unloaded state.

The pump chamber 20 has an inlet 26 and an outlet 28 which are each arranged at the end of a supplying or discharging channel structure 13. The supplying channel structure 13 comes from the cassette inlet 60 which can be connected to a fluid supply 40 by means of a sealing element 62. The sealing element 62 is in this connection shaped by an extension, preferably a ring-shaped extension, of the flexible first part 12 which passes through the rigid carrier structure 16. The fluid inflow 40 furthermore has a valve element 42 by means of which the inflow can be blocked. The direction of the inflowing fluid F is indicated by arrows.

The cassette outflow 70 is substantially made in the same construction as the inlet 60 and likewise has a sealing element 72 which is made in ring shape by the flexible first part 12. The fluid outflow 70 is in this connection connectable to the outflow channel 50, with the outflow channel 50 having a valve element 52 by means of which the outflow channel 50 can be blocked.

At the machine side, a support surface 100 is provided on which the carrier structure 16 can be placed. The support surface 100 is penetrated by the housing 110 of the means for the generation of a magnetic field. The means for the generation of a magnetic field is a coil 120 which is fully engaged around by the housing. The housing 110 furthermore has a receiver 114 which is adapted to the geometry of the pump membrane 21. The housing 110 furthermore has a hollow space 112 into which an iron core can optionally be inserted for the reinforcement of the magnetic field.

The operation of the system for pumping shown in the drawing figure can be made as follows in this respect: A magnetic field is applied by means of the electromagnet 120 so that the permanent magnet 30 is repulsed and is driven in the direction of the wall 14. At the same time, the valve element 42 must be closed to prevent a backflow movement and the valve element 52 must be open to enable an outflow of the fluid F. The pump membrane 21 restores itself automatically by switching off the magnetic field or the electromagnet 120. The valve element 52 is advantageously already closed at the moment of restoration and the valve element 42 is open so that the fluid F can again flow into the pump chamber 20. The valve 42 is then closed again and the valve 52 is opened and the magnetic field is applied by the electromagnet 120 so that a displacement of fluid from the pump chamber 20 again takes place by the repulsion of the permanent magnet 30.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

What is claimed is:

1. A disposable element comprising:
a first part that includes a flexible ration;
a second part sealingly covering the first part, with the flexible region of the first part forming, with the second part, a pump chamber;
a channel structure that leads to an inlet of the pump chamber; and
a rigid carrier structure,
with a first portion of the first part being bonded to the rigid carrier structure, and a second portion of the first part including the flexible region being arranged to extend through a cut-out of the rigid carrier structure,
with the second part being configured as a layer arranged on a side of the first part facing away from the rigid carrier structure, with the second part layer extending in a plane, from which the flexible region of the first part rises in dome-like form passing through the cut-out of the rigid carrier structure,
with the flexible region including at least one of a permanent magnet and a permanent magnetic region so that liquid is displaceable by the flexible region by application of a magnetic field to the flexible region,
with the rigid carrier structure being configured as a flat plane having a first side to which the first portion of the first part is bonded, and a second opposed side, with the cut-out extending through the carrier structure from the first side to the second side,
with the second portion of the first part that includes the flexible region extending through the cut-out of the carrier structure such that the dome-like form thereof extends beyond the second side of the carrier structure, and
with the rigid carrier structure and the first portion of the first part each being configured in layer form, with the first part being configured completely as a flexible material, and with the channel structure being a recessed region of the first portion of the first part.

2. The disposable element in accordance with claim 1, wherein the rigid carrier structure and the first part have a one piece two-component injection molding construction.

3. The disposable element in accordance with claim 1, wherein the pump chamber is an element of a membrane pump.

4. The disposable element in accordance with claim 1, wherein the flexible region includes the inlet and an outlet, with the inlet and the outlet each being connected to a respective inlet channel structure and outlet channel structure.

5. The disposable element in accordance with claim 1, wherein the permanent magnet is an insertion part which is completely encased by the flexible region.

6. The disposable element in accordance with claim 1, wherein at least one of the permanent magnet and the permanent magnetic region is arranged in a part of the flexible region that is disposed opposite a wall so that the at least one flexible region is movable in at least one of a direction of the wall by the application of the magnetic field with a first orientation and a direction away from the wall by the application of the magnetic field with a second orientation.

7. The disposable element in accordance with claim 1, wherein the flexible region has a peripherally concave side wall which has a diameter reducing toward a region of the flexible region that includes the at least one of the permanent magnet and the permanent magnetic region.

8. The disposable element in accordance with claim 7, wherein the side wall is resilient and opposes a pressing in of the flexible region with a resilient force which effects a self-restoration of the flexible region on load removal.

9. A system for pumping comprising a disposable element in accordance with claim 1, and
a blood treatment machine including a reception apparatus into which the disposable element is insertable, and an electromagnetic coil for generation of the magnetic field with which the flexible region of the disposable element inserted into the reception apparatus is movable for pumping a medical fluid.

10. The system in accordance with claim 9, wherein the reception apparatus engages around the disposable element in a shape-matched manner.

11. The system according to claim 9, wherein the electromagnetic coil has an iron core, and is arranged in a housing having a receiver for the flexible region.

12. The system in accordance with claim 9, wherein the electromagnetic coil is arranged in a housing of the reception apparatus including a receiver for the flexible region.

13. The system according to claim 12, wherein the blood treatment apparatus is a dialysis machine.

14. The system according to claim 12, wherein the system is an analysis unit.

15. The disposable element according to claim 1, wherein the channel structure is recessed in a surface of the first part facing the second part.

16. The disposable element according to claim 1, wherein the rigid carrier structure and the first part have a two-component injection molding construction, and wherein the second part is configured as an adhesion to the two-component injection molding construction.

17. The disposable element of claim 1, wherein the first portion of the first part bonded to the rigid carrier structure extends in a plane parallel to the flat plane of the carrier structure, and
wherein a surface area of the rigid carrier structure at which the rigid carrier structure is bonded to the first region of the first part is larger than a surface area of the cutout.

18. The disposable element according to claim 1, wherein the channel structure is arranged to extend between the first part and the second part and is recessed in a surface of the first part facing the second part.

19. A method of pumping a liquid, said method comprising
coupling a disposable element to a reception apparatus of a blood treatment machine, the blood treatment machine including an electromagnetic coil for generation of a magnetic field, the disposable element having a first part that includes a flexible region, a second part sealingly covering the first part, with the flexible region of the first part forming, with the second part, a pump chamber, a channel structure that leads to an inlet of the pump chamber, and a rigid carrier structure, with a first portion of the first part being bonded to the rigid carrier structure, and a second portion of the first part including the flexible region being arranged to extend through a cut-out of the rigid carrier structure, with the second part being configured as a layer arranged on a side of the first part facing away from the rigid carrier structure, with the second part layer extending in a plane, from which the flexible region of the first part rises in dome-like form passing through the cut-out of the rigid carrier structure, with the flexible region including at least one of a permanent magnet and a permanent magnetic region so that liquid is displaceable by the flexible region by application of a magnetic field to the flexible region, and with the rigid carrier structure and the first portion of the first part each being configured in layer form, with the first part being configured completely as a flexible material, and with the channel structure being a recessed region of the first portion of the first part; and displacing the liquid with the flexible region by applying a magnetic field thereto.

20. The method according to claim 19, wherein the liquid is a medical liquid.

* * * * *